United States Patent [19]

Hagemeyer et al.

[11] Patent Number: 5,689,005
[45] Date of Patent: Nov. 18, 1997

[54] REDUCTIVE DEOXYGENATION USING A REDOX CATALYST

[75] Inventors: Alfred Hagemeyer, Ludwigshafen; Christopher William Rieker, Mannheim; Thomas Lautensack, Altleiningen; Dieter Hermeling, Böhl-Iggelheim, all of Germany

[73] Assignee: BASF Aktiengesellschaft, Ludwigshafen, Germany

[21] Appl. No.: 563,627

[22] Filed: Nov. 28, 1995

[30] Foreign Application Priority Data

Dec. 6, 1994 [DE] Germany ............... 44 43 360.3

[51] Int. Cl.⁶ .................................................. C07C 209/36
[52] U.S. Cl. ................... 564/420; 568/17; 568/8; 568/38; 568/61; 568/949
[58] Field of Search .......................... 568/8, 17, 38, 568/61, 949; 564/401, 416, 420

[56] References Cited

U.S. PATENT DOCUMENTS

| | | | |
|---|---|---|---|
| 3,118,007 | 1/1964 | Kroenig et al. | 585/617 |
| 3,354,212 | 11/1967 | Donaruma | 564/261 |
| 3,440,299 | 4/1969 | Woskow et al. | 585/444 |
| 3,780,111 | 12/1973 | Young et al. | 568/17 |
| 4,396,537 | 8/1983 | Eastman | 252/437 |
| 4,644,089 | 2/1987 | Lee | 585/407 |
| 4,668,802 | 5/1987 | Contractor | 549/259 |
| 4,727,193 | 2/1988 | Dockner | 568/8 |
| 4,959,202 | 9/1990 | Minet et al. | 423/502 |

FOREIGN PATENT DOCUMENTS

| | | |
|---|---|---|
| 0 005 747 | 12/1979 | European Pat. Off. . |
| 0 030 837 | 6/1981 | European Pat. Off. . |
| 0 548 682 | 6/1993 | European Pat. Off. . |
| 26 38 720 | 3/1977 | Germany . |
| 840082 | 7/1960 | United Kingdom . |
| 885422 | 12/1961 | United Kingdom . |

*Primary Examiner*—Brian M. Burn
*Attorney, Agent, or Firm*—Oblon, Spivak, McClelland, Maier & Neustadt, P.C.

[57] ABSTRACT

A process for the deoxygenation of organic oxo compounds, in particular phosphine oxides to phosphines and nitrobenzene to aniline, with reduced redox catalysts in a non-steady-state reaction with decoupled reductive regeneration of the redox catalyst entails the redox catalyst being reduced to a lower oxidation state and being reused for the deoxygenation.

9 Claims, 2 Drawing Sheets

5,689,005

REDUCTIVE DEOXYGENATION USING A REDOX CATALYST

BACKGROUND OF THE INVENTION

1. Field of the Invention

The invention relates to a process for the reductive deoxygenation, with heterogeneous catalysis, of organic compounds which contain an oxo group which is difficult to reduce, in particular of phosphine oxides to the corresponding phosphines, and of nitrobenzene to aniline.

2. Description of the Background

Deoxygenations of organic compounds containing oxo groups represent an important class of reactions in organic chemistry for the synthesis or regeneration of oxidized reagents.

Examples are the reduction of phosphine oxides to the corresponding phosphines, the deoxygenation of esters to ethers, the reduction of aliphatic and aromatic nitro compounds to the nitroso compounds, oximes or amines, in particular the reduction of nitrobenzene to aniline, and the reduction of sulfonic acids to mercaptans.

The reduction of triphenylphosphine oxide (TPPO) to triphenylphosphine (TPP) is a particular industrial problem. TPP is frequently used in organic chemistry for Wittig reactions to form C=C double bonds (eg. in vitamin A synthesis), in which case TPPO is formed as reaction product or, more accurately, waste product and is usually then incinerated. On the other hand, reduction of TPPO to TPP and reuse thereof will complete the circulation of materials, reduce the amounts of waste and save incineration capacity.

The same applies to the use of TPP as cocatalyst in hydroformylations and the recovery of tricyclohexylphosphine from tricyclohexylphosphine oxide.

Direct reduction of TPPO to TPP, for example with $H_2$ or CO, ie. applying the conventional steady-state reaction with the conventional and available reducing agents, often does not succeed or affords only low conversions because the thermodynamic stability of TPPO is considerably higher than that of TPP, and the chemical equilibrium is therefore far over to the side of TPPO. TPPO reduction with metallic reducing agents can therefore be carried out (in a steady-state reaction) only with very oxophilic metals (eg. metallic Al) which, however, are converted thereby into salts of little value (eg. oxides or halides). The latter are, however, so stable that recycling thereof to the metals can be carried out only at considerable expense. Steady-state reduction of phosphine oxides via the dihalide with strong reducing agents has been described several times. Thus, according to U.S. Pat. No. 3,780,111, the phosphine oxide is initially converted into the dihalide which is then reduced with Fe. EP 548 682 describes the reduction of phosphine oxides or of phosphine dihalides (obtained therefrom by, for example, phosgenation) with Si or Si alloys. Dehalogenation of $TPPCl_2$ with Na is described in DE-A-2 638 720, and that with white phosphorus is described in G. Wunsch et al., Allgem. Chem. 369 (1969) 33. EP 005 747 relates to the liquid-phase catalytic hydrogenation of $TPPCl_2$ with $H_2$ using Pt, Pd, Rh, Ru and/or Ir catalysts. U.S. Pat. No. 4,727,193 deals with the liquid-phase reduction of phosphine oxides or dihalides with a hydrocarbon in the presence of active carbon at elevated temperatures. A reaction medium comprising white oil, carbon powder and TPPO affords after reaction at 350° C. for 6 h a 52% conversion and 68% selectivity to TPP. The advantage of the low-cost reagents is in this case counteracted by the disadvantage of the low space-time yield and long reaction times; in addition, there is always the problem in liquid-phase reactions, in contrast with gas-phase reactions, of removing the catalyst and/or the product (eg. by distillation, extraction etc.), so that more elaborate workup is necessary.

It is an object of the present invention to propose a process which permits the reduction in an advantageous manner, using regenerable reagents or catalysts, of oxo compounds which are difficult to reduce. It is a particular object to convert phosphine oxides into the corresponding phosphines avoiding the route through the corrosive dihalides and the production of salt associated therewith.

SUMMARY OF THE INVENTION

We have found that this object is achieved by a process for the reductive deoxygenation of organic compounds which contain at least one oxo group with partial or complete formation of the corresponding deoxygenated compounds by reaction with heterogeneous catalysis by redox catalysts in their reduced or partially reduced form at elevated temperature in the gas phase, wherein a) the deoxygenation is carried out continuously in temporal or spatial alternation with the reducing regeneration of the redox catalyst, and this is carried out as a non-steady-state reaction, ie. the organic compounds to be deoxygenated are contacted with the redox catalyst in such a way that catalyst with unused deoxygenating activity is still present at the exit from the deoxygenation zone, and wherein b) the regeneration of the used redox catalyst is carried out with gaseous reducing agents selected from the group consisting of hydrogen, carbon monoxide, hydrocarbons, ammonia, nitrogen monoxide and sulfur dioxide at elevated temperature, and c) a redox catalyst which contains in its oxidized form at least one reducible oxide, of the metals selected from the group consisting of Bi, V, Cr, Mn, Ti, Fe, Co, Pb, Mo, Ce, U, Sn, Sb and/or Cu is used.

DETAILED DESCRIPTION OF THE DRAWINGS

Figure 1:
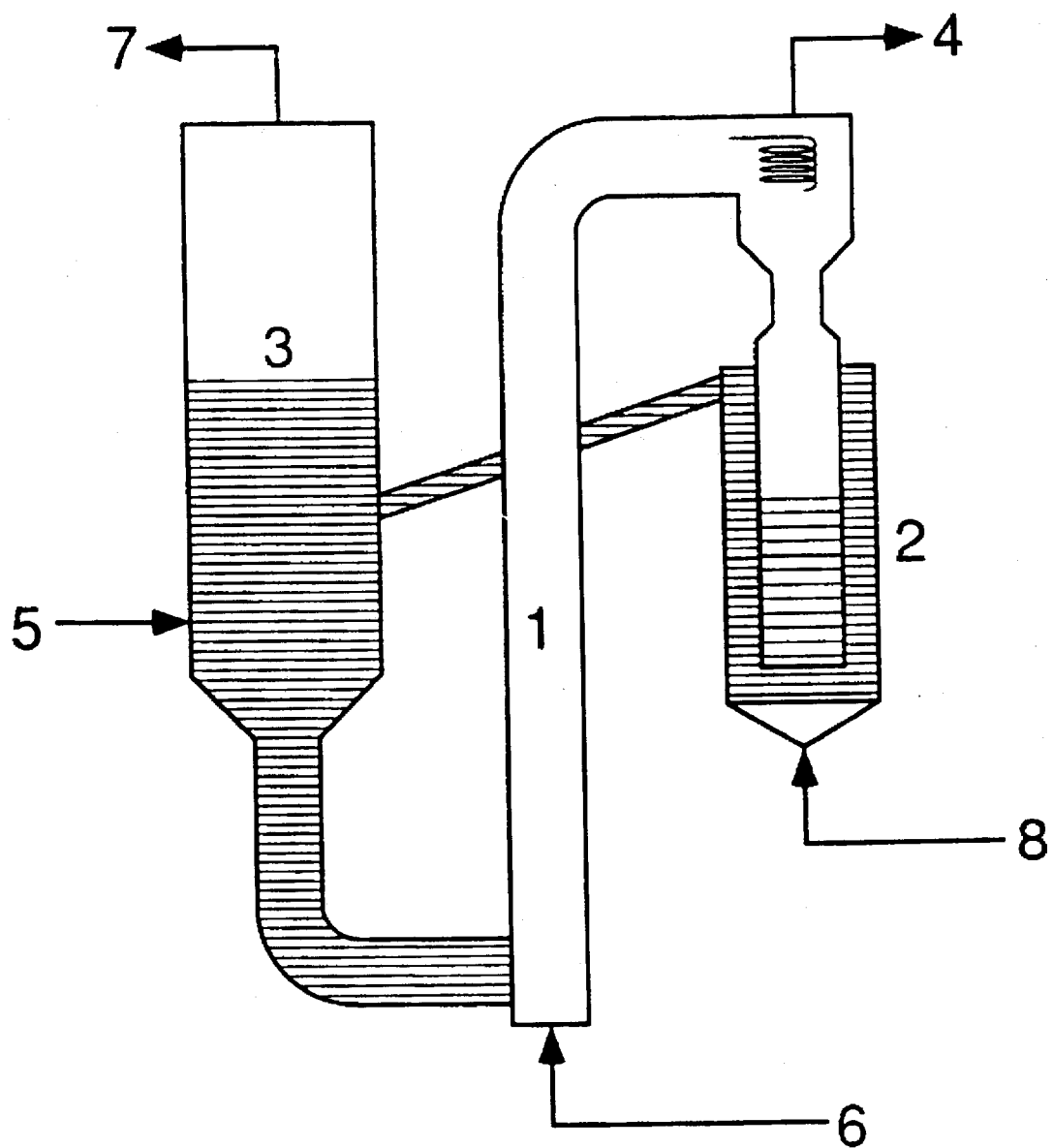
Figure 2:
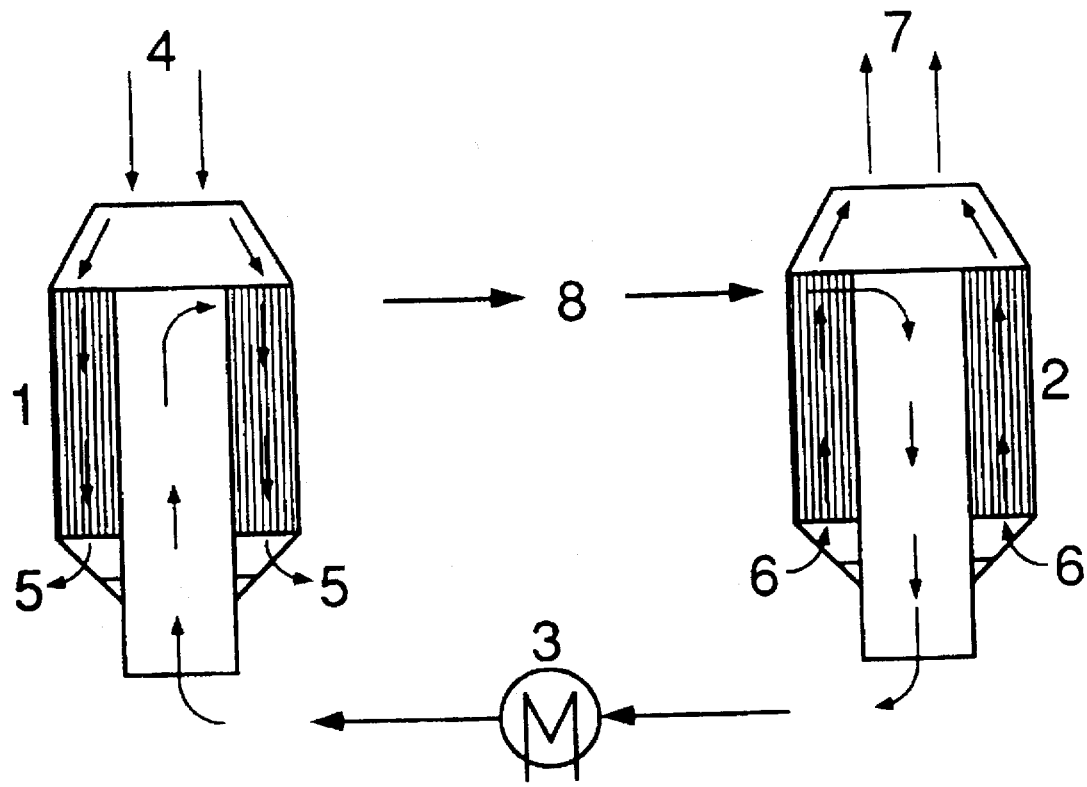

FIGS. 1 and 2 show alternate embodiments of the invention, i.e., spatial separation, and temporal separation, respectively, of the two steps.

DETAILED DESCRIPTION OF THE INVENTION

In the novel reaction, the reduced redox catalyst acts both as catalyst and as oxygen acceptor and is thus converted into a higher oxidation state and must be reduced again in a temporally or spatially separate regeneration so that, as a rule, at least stoichiometric amounts of the redox catalyst are required for the deoxygenation. However, in some cases, it is also possible to carry out the deoxygenation in the presence of reducing gases so that, in these cases, less than the stoichiometric amounts of catalyst are required.

There are two variants for the industrial implementation of the non-steady-state reaction concept, namely either the spatial or the temporal separation of the two steps.

In the former case, a moving bed or a circulating fluidized bed, for example, is used with a riser reactor so that the catalyst particles are conveyed out of the deoxygenation zone, after removal of the reaction products, to a separate regeneration reactor in which the catalyst is reduced. The regenerated catalyst is returned to the deoxygenation zone.

The process is continuous and cyclic because the catalyst is continuously circulated. The catalyst is exposed to great mechanical stress during this and must therefore have adequate hardness. This embodiment is depicted diagrammatically in FIG. 1. In this, 1 is the riser, 2 is the separation of the deoxygenated product 4 from the used catalyst and 3 is the regenerator where the used catalyst is reduced again after charging with reducing agent 5.

The precursor to be deoxygenated enters at 6, and the off-gas leaves the system at 7, while inert gas is fed in at 8.

A temporal separation can be implemented in a fixed bed of catalyst, preferably a tubular reactor, in which essentially no backmixing takes place, in such a way that the reactor is periodically charged, by switching over, with the compound to be deoxygenated and the regenerating gas, it also being possible for an intermediate flushing with inert gas to take place. When a plurality of reactors is used, the switching over or switching further takes place in a particularly simple manner so that the deoxygenation reaction and the regeneration can take place continuously and in parallel. This is illustrated in FIG. 2. This depicts fixed bed reactors designed as tube bundle reactors. While the actual deoxygenation reaction is taking place in reactor 1 and product is being generated, the regeneration of the used redox catalyst with reducing agent is just taking place in reactor 2. 3 is a heat exchanger. In this case, the precursor to be deoxygenated is fed in at 4 and leaves, as product free of oxo groups, the reactor at 5. In the regeneration reactor 2, the reducing agent (regenerating gas) enters at 6 and leaves the reactor as off-gas at 7. 8 is a heat coupling.

The non-steady-state reaction, ie. the avoidance of an equilibrium being set up by maintaining a reaction gradient, in this case the gradient of the reducing activity of the redox catalyst with avoidance of back-mixing, is achieved by maintaining pipe (plug) flow and maintaining still sufficient reducing activity of the catalyst at the exit from the deoxygenation zone.

The redox catalyst to be used in the process according to the invention comprises in its oxidized form at least one reducible active metal oxide of the metals, selected from the group consisting of Bi, V, Cr, Mn, Ti, Fe, Co, Pb, Mo, Ce, U, Sn, Cu, which can be used either as pure oxide or metal or applied to a support. The nature of the support is not in general subject to any restrictions as long as it is inert and has the necessary mechanical strength. As a rule, it is selected from the group consisting of clays, PILC (pillared clays), zeolites, aluminum phosphates, SiC, $Si_3N_4$, BN, C, and/or of the metal oxides selected from the group of oxides of Ti, Zr, Zn, Th, Mg, Ca, Ba, Si, Al. The redox catalyst can also contain further promoters, in particular alkali (alkaline earth) and/or rare earth metals. Supported catalysts have the advantage of high mechanical stability in respect of the continuous phase and structural transformations of the active component. The active component loading is in the range from 2 to 95% by weight, calculated on the basis of active metal oxide.

The catalyst can be prepared by all known processes, eg. by dry mixing, impregnation, saturation, precipitation, coprecipitation, spray drying, spray impregnation, evaporation. Suitable catalyst precursors are the oxides, hydroxides, carbonates, nitrates, complex compounds with inorganic or organic chelating agents, salts of inorganic and organic acids and organometallic compounds.

These catalyst precursors are converted by a suitable heat treatment, usually together with the reducing activation, into the active catalyst form.

It is evident that an activity of the systems in respect of deoxygenation is present only if the active metal is not in its highest oxidation state but is in at least partially reduced form. In the case of Bi as active metal, the Bi oxides formed by oxygen uptake during the deoxygenation are reduced virtually to metallic Bi with $H_2$ at from 300° to 500° C. The active phase at the start of the reaction is then finely divided Bi metal on a support with a large surface area. As the deoxygenation reaction progresses, the catalyst is increasingly oxidized by oxygen uptake and thus loses activity, and the conversion falls. As a consequence of this inactivation, the yield of deoxygenation product as a function of the reaction time generally passes through a flat maximum or a plateau and then falls steadily. In industry there will not be continuation until the catalyst is completely inactivated, on the contrary the regeneration will be initiated beforehand, when the yield or the conversion has fallen to a particular value, for example, when the yield has fallen by 10 to 20% below the maximum. The change, which is the maximum possible at the particular reaction temperature, in the oxidation state of the active metal (eg. Bi(O)<-->Bi(III) or V(III)<-->V(V) at≈500° C.) thus does not take place completely, on the contrary degrees of catalyst utilization less than 1 are expedient.

The catalyst is used as particulate catalyst in the fixed bed, eg. in the form of extrudates, rings, annular tablets, granules or chips, beads, whole tablets or meshes with dimensions from 0.5 to 20 mm.

On the other hand, for use of the catalyst in a moving bed or fluidized bed, fine particles of high mechanical strength in the size range from 0.01 to 0.9, preferably 0.05 to 0.5, mm are indicated.

The deoxygenations by the process according to the invention are carried out at from 100° to 1000° C., with holdup times of from 0.01 to 100 s, under pressures from 100 mbar to 100 bar and with a WHSV (Weight Hourly Space Velocity) from 0.01 to 20 (kg of compound to be deoxygenated/kg of cat.) $\times h^{-1}$. Besides the precursor to be deoxygenated, the feed may contain diluents such as $CO_2$, $N_2$, inert gases or steam or else the regenerating gas (reducing agent) itself. In the specific case of the reduction of phosphine oxides, the reaction is carried out at from 400° to 800° C. with a holdup time of from 0.5 to 20 s, under pressures from 0.5 to 10 bar and with a WHSV of from 0.05 to 10 $h^{-1}$.

The regeneration (reduction) of the used, partially oxidized catalyst is carried out at temperatures in the range 100°–1000° C. with a free reducing agent, preferably with hydrocarbons, in particular low molecular weight saturated hydrocarbons, with $NH_3$, NO or $SO_2$ and, particularly preferably, with $H_2$ and/or CO. Diluents can also be present in the inflow into the reactor in this instance. The regeneration can be carried out under subatmospheric, atmospheric or superatmospheric pressure. Pressures in the range from 100 mbar to 20 bar are preferred.

Also suitable as regenerating gases are reactive gas mixtures which liberate the actual reducing agent only in the reactor by chemical reaction. Thus, for example, the catalyst can be additionally doped with Cu, and $CO/H_2O$ can be used as regenerating gas. An in situ conversion reaction on the Cu center then forms $H_2$ which is able to reduce the metal oxide.

Although the novel process can be applied to any organic compounds which contain oxo groups which are difficult to reduce, it is particularly suitable for the deoxygenation of esters to ethers, nitro compounds to the nitroso compounds, oximes or amines, sulfonic acids to mercaptans and, in particular, of phosphine oxides to phosphines or of nitrobenzene to aniline.

Accordingly, phosphine oxides of the general formula $R^1R^2R^3P=O$ can be reduced to phosphines of the general formula $R^1R^2R^3P$, where $R^1$, $R^2$, $R^3$ are, independently of one another, an unsubstituted or substituted $C_1$ to $C_8$, preferably $C_1$ to $C_6$, alkyl radical an unsubstituted or substituted $C_1$ to $C_{12}$, preferably $C_1$ to $C_8$, cycloalkyl radical or an unsubstituted or substituted phenyl radical of the formula

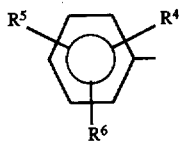

where $R^4$, $R^5$, $R^6$ are, independently of one another, hydrogen, $C_1$–$C_4$-alkyl, $C_1$–$C_4$-alkoxy, fluorine, chlorine, bromine, COOH or $COOR^7$ where $R^7$ is $C_1$–$C_4$-alkyl.

Particularly preferred starting compounds are
trimethylphosphine oxide
triethylphosphine oxide
tributylphosphine oxide
tricyclopentylphosphine oxide
tricyclohexylphosphine oxide
tritolylphosphine oxide
tri(tert-butylphenyl)phosphine oxide
tri(isopropylphenyl)phosphine oxide
tri(methoxyphenyl)phosphine oxide
tolyldiphenylphosphine oxide
phenylditolylphosphine oxide
methyldibutylphosphine oxide
and, in particular, triphenylphosphine oxide.

A non-steady-state reaction has been described previously for a large number of oxidation and dehydrogenation reactions:

In these cases the oxidation/dehydrogenation reaction is carried out in the absence of free oxidizing agent, ie. without continuous addition thereof to the precursor stream, such as molecular oxygen or oxygen-containing gases and, instead, the redox catalyst which comprises at least one reducible supported metal oxide acts as the sole oxygen source and thus assumes the function of an oxygen store. The oxide catalyst is reduced, owing to the release of lattice oxygen, during the oxidation/dehydrogenation and is therefore consumed during the course of the reaction so that it has to be regenerated by reoxidation in a second step using an oxidizing agent, preferably oxygen-containing gases, including pure oxygen.

This general reaction concept for separating the two oxidation reaction steps using a reducible and regenerable catalyst as true reactant has been described previously, for example, for the oxidation and ammonoxidation of propene to acrolein and acrylic acid, and acrylonitrile, respectively (GB 885422; GB 999629; K. Aykan, J. Catal. 12 (1968) 281–190) using arsenate and molybdate catalysts. The use of the process for the oxidative dehydrogenation of aliphatic alkanes to mono- and diolefins with ferrite catalysts (eg. U.S. Pat. No. 3,440,299, DE 2 118 344, DE 1 793 499; and U.S. Pat. No. 3,118,007) is likewise prior art. According to GB 840 082, Fe, Co, Ni oxides are used as solid oxygen donors for the oxidative dehydrogenation of mono- to diolefins. Numerous patents have described precisely this process for the oxidative coupling of methane to higher hydrocarbons, using various classes of catalysts (eg. U.S. Pat. No. 4,795,849, DE 3 586 769 with Mn/Mg/Si oxides; U.S. Pat. No. 4,568,789 with Ru oxide; EP 25 44 23 with Mn/B oxides on MgO; GB 2 156 842 with $Mn_3O_4$ spinels). The dehydrodimerization of toluene to stilbene, likewise in the absence of free oxygen, using reducible catalysts such as Bi/In/Ag oxides (EP 30 837) is also known. Finally, the same principle is also applied to the dehydrogenation, dehydrocyclization and dehydroaromatization of lower alkane mixtures for petroleum upgrading (U.S. Pat. No. 4,396,537 with Co/P oxide catalysts and U.S. Pat. No. 4,644,089 with $V_2O_5$/aluminium phosphates). Finally, JP A2 60/25938 describes very generally oxidation and dehydrogenation reactions with solid oxide oxygen donors.

In the applications EP 397 637 and EP 403 462, the abovementioned process principle is used for the oxidative dehydrogenation of aliphatic and alkylaromatic compounds. The particularly preferred redox catalyst is V/MgO. More recent patent applications contain the $B_2O_3$ doping of solid oxygen donors in the form of reducible metal oxides and the application thereof to the oxidative coupling of methane, the oxidative dehydrogenation of alkanes (EP 254 423), and the oxidative dehydrogenation of alkanes and alcohols with $Au/CeO_2$ (EP 558 148). Maleic anhydride synthesis from n-butane in a riser-regenerator reactor is explained in U.S. Pat. No. 4,668,802.

The scientific literature also contains discussions of non-steady-state oxidation reactions. Doroschenko et al., Neftechimia 26 (1986) 48 investigate the non-steady-state oxidative dehydrogenation of butane with V-Mg-Mo-O systems. Moreover Ogonowski, Chemik XLII 3 (1989) 68, deals with the dehydrogenation of butane with V-Mg-Mo-O/MgO and Mo-Co-O/MgO catalysts.

Non-steady-state Deacon processes for producing chlorine by the atmospheric oxidation of HCl are disclosed in DE 40 04 454, U.S. Pat. No. 4,959,202 and WO 91/06505 or U.S. Pat. No. 5,154,911.

All the non-steady-state processes previously described relate, where they are used for carrying out chemical redox reactions with decoupling of the reaction steps, without exception to oxidation or dehydrogenation reactions. The redox catalyst acts as oxygen store. The precursor is oxidized by lattice oxygen. During this the oxygen is incorporated into the precursor molecule, or water is formed (oxidative dehydrogenations).

The said comprehensive literature on oxidation processes, and the complete absence of corresponding literature on relevant reduction processes, shows that it was evidently not obvious to propose such a reduction process, especially since the need for a suitable process, at least for reducing phosphine oxides, has existed for a long time. Accordingly, a prejudice has been overcome by the novel deoxygenation process, and a novel method for deoxygenation has been revealed.

Another technical problem which can be surprisingly advantageously solved with the aid of the process according to the invention is the deoxygenation of nitrobenzene to aniline. The non-steady-state reductive deoxygenation of nitrobenzene in the gas phase on previously reduced supported metal (oxide) redox catalysts as regenerable solid reductants has not yet been disclosed. The advantages of this type of deoxygenation are that, in the final analysis, very low-cost reducing agents such as CO or $H_2$ can be used, that high pressure is not necessary, that operating safety is much higher due to the spatial or temporal separation of reducing agent (CO or $H_2$) and oxidizing agent (nitrobenzene), and that there is great resistance to catalyst poisons due to the very high active metal loading (preferably about 10–30% by weight Bi). An additional point when Bi is the catalyst metal is that Bi is liquid at the reaction temperature and is therefore repeatedly circulated so that the active catalyst surface is continually renewed.

EXAMPLE 1

Catalyst preparation 100 g of $TiO_2$ (Rhone-Poulenc type DT-51) and 64.6 g of basic Bi carbonate $Bi_2CO_5$ (Merck, contains 81% by weight Bi) were mixed in the dry for one hour (h). The mixture was compacted in a kneader for 2.5 h. During the kneading phase, 3% by weight of organic extruding auxiliary and 107 ml of water were added. The kneaded composition was extruded to 3 mm solid pellets in an extruder. These were dried in a circulating air dryer at 120° C. for 2 h and then calcined at 500° C. for 2 h.

The catalyst contained 37% by weight $Bi_2O_3$ and 63% by weight $TiO_2$. The Bi/$TiO_2$ catalyst has a high mechanical (cutting) hardness of 33.6 N/strand and a BET surface area of 49.2 m$^2$/g. A 0.5–0.71 mm chip fraction is used for the deoxygenation.

Deoxygenation reaction and regeneration of the catalyst

The TPPO reduction was carried out in a salt bath/fixed bed reactor. The latter was a coil reactor which had a ratio of the length of the pipe to the internal diameter of the pipe of 70 cm to 6 mm and which was charged with the catalyst which had previously been reduced with hydrogen at 500° C. TPPO was fed in continuously as a 6% strength solution in toluene, and the reduction was carried out at 500° C. with a holdup time of 2 s. The product gases were condensed at −4° C.

As soon as the instantaneous yield of TPP fell below 20% of theory, flushing with $N_2$ was carried out and reduction with hydrogen was carried out at 500° C.

The reduction was complete after 1 h and was followed by a new deoxygenation cycle.

A mixture of 72% TPP and 28% TPPO was obtained, and the TPP was removed from this in a conventional way, eg. by distillation.

EXAMPLE 2

Catalyst preparation 14.57 g of $Bi(NO_3)_3 \times 5H_2O$ were dissolved in 10 ml of concentrated $HNO_3$ and distilled water and then made up to a total of 65 ml of solution. The solution was then divided and 93 g of $TiO_2$ support (4 mm strands, water uptake=0.35 ml/g) were impregnated twice with the Bi nitrate solution.

The strands were then dried at 120° C. for 16 h and calcined at 500° C. for 2 h.

The catalyst contained 10% by weight $Bi_2O_3$ and 90% by weight $TiO_2$. It had a high mechanical (cutting) hardness of 31 N/strand and a BET surface area of the finished catalyst of 56.7 m$^2$/g.

Deoxygenation and regeneration of the catalyst

The experiments on the reductive deoxygenation of nitrobenzene were carried out in a coiled tube reactor with a catalyst volume of 20 ml with temperature control by an external liquid salt melt so that conditions were approximately isothermal. The catalyst comprised a 0.5–0.71 mm chip fraction.

The fixed catalyst bed was previously reduced at the reaction temperature with $H_2$ for 1 h and then flushed with $N_2$. Then a mixture of nitrobenzene and n-butanol (as hydrogen donor) in $N_2$ carrier gas was passed over the bed, followed by flushing with $N_2$. This cycle of catalyst reduction with $H_2$ and nitrobenzene reduction was repeated indefinitely.

The cumulative liquid discharge from the reactor was collected in a cold trap and analyzed after each cycle by GC. The reaction conditions such as temperature, holdup time (HT) and time, and the reactor results are shown in the following Table, in which the products are indicated in percentage areas. The difference from 100% derives from byproducts. It is evident that aniline can be obtained in good yields with quantitative nitrobenzene conversions.

TABLE

| Experiment | Temperature [°C.] | HT [sec] | Reaction time [min] | Nitrobenzene: butanol ratio in $N_2$ [mol/mol] | Products | | |
|---|---|---|---|---|---|---|---|
| | | | | | Nitrobenzene [% by wt] | Butanol [% area] | Aniline [% area] |
| 1 | 400 | 3.6 | 60 | 1:1 | 1.15 | — | 97.14 |
| 2 | 400 | 3.6 | 30 | 1:1 | 1.59 | 0.3 | 88.13 |
| 3 | 400 | 3.6 | 30 | 1:1 | 0.5 | 0.9 | 90.3 |
| 4 | 350 | 3.9 | 30 | 1:1 | — | — | 44.0 |
| 5 | 350 | 3.9 | 30 | 1:1 | — | — | 44.1 |
| 6 | 350 | 3.9 | 30 | 1:1 | — | — | 40.4 |
| 7 | 400 | 2.3 | 30 | 2:1 | — | 0.7 | 58.3 |
| 8 | 400 | 2.3 | 30 | 2:1 | — | 1.6 | 79.1 |
| 9 | 400 | 2.3 | 30 | 1:2 | — | — | 34 |
| 10 | 400 | 2.3 | 30 | 1:2 | — | 12.6 | 7.4 |
| 11 | 300 | 2.6 | 30 | 1:1 | 9.6 | 66.7 | 11.2 |

We claim:

1. A process for reductive deoxygenation of an organic compound which contains at least one oxo group with partial or complete formation of a corresponding deoxygenated compound by reaction with heterogeneous catalysis by a redox catalyst in its reduced or partially reduced form at elevated temperature in the gas phase, and reductive regeneration of the redox catalyst, comprising carrying out the deoxygenation continuously in a deoxygenation zone containing an outlet, in temporal or spatial alternation with the reductive regeneration of the redox catalyst, and the deoxygenation is carried out as a non-steady-state reaction, wherein the organic compound to be deoxygenated is contacted with the redox catalyst in such a way that catalyst with unused deoxygenating activity is still present at the outlet from the deoxygenation zone, wherein the regeneration of the redox catalyst is carried out with a gaseous reducing agent selected from the group consisting of hydrogen, carbon monoxide, hydrocarbons, ammonia, nitrogen monoxide and sulfur dioxide at elevated temperature, and the redox catalyst contains in its oxidized form at least one reducible oxide of the metals selected from the group consisting of Bi, V, Cr, Mn, Ti, U, Fe, Co, Pb, Mo, Ce, Sn, Sb and Cu.

2. A process as claimed in claim 1, wherein a temporal alternation of the redox reaction takes place in such a way that a fixed bed of catalyst is used and is charged periodically, by switching over, with the compound to be deoxygenated and the gaseous reducing agent.

3. A process as claimed in claim 1, wherein a spatial decoupling of the deoxygenation and the catalyst reduction takes place in such a way that movable catalyst particles are circulated between a deoxygenation reactor and a separate regeneration reactor using a moving bed or a circulating fluidized bed.

4. A process as claimed in claim 1, wherein a deoxygenation of phosphine oxides to phosphines, esters to ethers, nitro compounds to the nitroso compounds, oximes or amines, sulfonic acids to mercaptans, or nitrobenzene to aniline is carried out.

5. A process as claimed in claim 1, wherein a deoxygenation of phosphine oxides of the formula $R^1R^2R^3P=O$ to the corresponding phosphines is carried out, where $R^1$, $R^2$ and/or $R^3$ are low molecular weight alkyl, cycloalkyl or aryl radicals.

6. A process as claimed in claim 1, wherein triphenylphosphine oxide, tricyclohexylphosphine oxide or tributylphosphine oxide is deoxygenated to the corresponding phosphines.

7. A process as claimed in claim 1, wherein a supported catalyst which contains as active metal bismuth, titanium or vanadium in an amount of from 2 to 95% by weight, calculated on the basis of $Bi_2O_3$, $TiO_2$ or $V_2O_5$, is used as redox catalyst.

8. A process as claimed in claim 6, wherein the deoxygenation reaction is carried out at from 400° to 1000° C. and under from 100 mbar to 100 bar.

9. A process as claimed in claim 1, wherein nitrobenzene is deoxygenated to aniline.

* * * * *